(12) United States Patent
Giardiello et al.

(10) Patent No.: US 10,500,066 B2
(45) Date of Patent: Dec. 10, 2019

(54) DEVICE FOR REMOVING AN ACETABULAR CUP

(71) Applicant: MEDACTA INTERNATIONAL SA, Castel San Pietro (CH)

(72) Inventors: Mirko Giardiello, Senna Comasco (IT); Massimiliano Bernardoni, Figino (CH); Francesco Siccardi, Sonvico (CH); Alberto Siccardi, Sonvico (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 422 days.

(21) Appl. No.: 15/302,025

(22) PCT Filed: Apr. 3, 2015

(86) PCT No.: PCT/IB2015/052457
§ 371 (c)(1),
(2) Date: Oct. 5, 2016

(87) PCT Pub. No.: WO2015/155657
PCT Pub. Date: Oct. 15, 2015

(65) Prior Publication Data
US 2017/0202681 A1    Jul. 20, 2017

(30) Foreign Application Priority Data

Apr. 8, 2014   (IT) .............................. MI2014A0645

(51) Int. Cl.
*A61F 2/46*        (2006.01)
*A61F 2/30*        (2006.01)

(52) U.S. Cl.
CPC .. *A61F 2/4609* (2013.01); *A61F 2002/30494* (2013.01); *A61F 2002/30565* (2013.01); *A61F 2002/4619* (2013.01)

(58) Field of Classification Search
CPC ............................. A61F 2/4609; B25B 13/466
See application file for complete search history.

(56) References Cited

U.S. PATENT DOCUMENTS

| 572,800 | A | * | 3/1896 | Henry | .................. B25B 13/466 |
| | | | | | 81/58.3 |
| 4,729,270 | A | * | 3/1988 | Pritchard | ................ B25B 13/00 |
| | | | | | 81/177.5 |
| 5,830,215 | A | | 11/1998 | Incavo et al. | |
| 6,565,575 | B2 | * | 5/2003 | Lewis | ................ A61B 17/1666 |
| | | | | | 606/99 |
| 7,998,146 | B2 | | 8/2011 | Anderson | |

(Continued)

OTHER PUBLICATIONS

Japanese Patent Office, Japanese Office Action, dated Jan. 8, 2019, 5 pages.

*Primary Examiner* — Andrew Yang
(74) *Attorney, Agent, or Firm* — Ference & Associates LLC

(57) ABSTRACT

A device is for removing an acetabular cup. The device may include a central body having a first end integrally connected to the central body, bearing a handle, and a transverse handle, and a second end integrally connected to the central body. The device may include a first toothed element, and a second toothed element coupled so that the second toothed element is configured to rotate by the first toothed element when the first toothed element rotates in a previously defined direction.

6 Claims, 3 Drawing Sheets

(56) References Cited

U.S. PATENT DOCUMENTS

| | | |
|---|---|---|
| 2006/0200165 A1 | 9/2006 | Tulkis |
| 2008/0195111 A1 | 8/2008 | Anderson |
| 2011/0130763 A1 | 6/2011 | Aux Epaules et al. |
| 2012/0184964 A1 | 7/2012 | Hudak, Jr. et al. |

* cited by examiner

DEVICE FOR REMOVING AN ACETABULAR CUP

RELATED APPLICATION

This application is based upon prior filed copending International Application No. PCT/IB2015/052457 filed Apr. 3, 2015, which claims priority to Italian Application No. MI2014A000645, filed Apr. 8, 2014, the entire subject matter of these applications is incorporated herein by reference in its entirety.

TECHNICAL FIELD

The present disclosure is directed to a medical device, and more particularly, to a device for removing an acetabular cup and related methods.

BACKGROUND

In the orthopedic field, there is increasingly a need for surgery to solve musculoskeletal apparatus disorders. In particular, there has been a great focus on curing diseases that can lead to motor difficulties for the patient such as, for example, deterioration of the hip joint. In fact, following diseases or simple deterioration due to the passing of time, the cartilaginous part of the hip joint can be consumed leading to contact between two bone surfaces that can generate pain.

In this case, through surgery, the diseased joint is replaced by inserting foreign parts into the skeletal structure able to effectively replace the original bone structures and perform their task. In the case of hip prostheses, the head of the femur and the acetabular cup are replaced through similar shaped implants and having similar tasks that are guaranteed to the patient's surrounding bone structure.

However, it is known that in the state of the art, the prostheses have an effective life that can rarely accompany the patient for their entire lifetime, especially if the patient has not undergone surgery at an advanced age. Therefore, when the prostheses are worn, they must be surgically replaced. The surgical operation usually envisions the removal of the acetabular cup and its replacement. Since the acetabular cup of the first implant is solidly joined to the patient's bone structure, the acetabular cup must be removed using suitable removal devices.

SUMMARY

Generally speaking, a device is for removing an acetabular cup. The device may include a central body having a first end integrally connected to the central body, bearing a handle, and a transverse handle, and a second end integrally connected to the central body. The device may include a first toothed element, and a second toothed element coupled so that the second toothed element is configured to rotate by the first toothed element when the first toothed element rotates in a previously defined direction.

DETAILED DESCRIPTION

Figure 1:
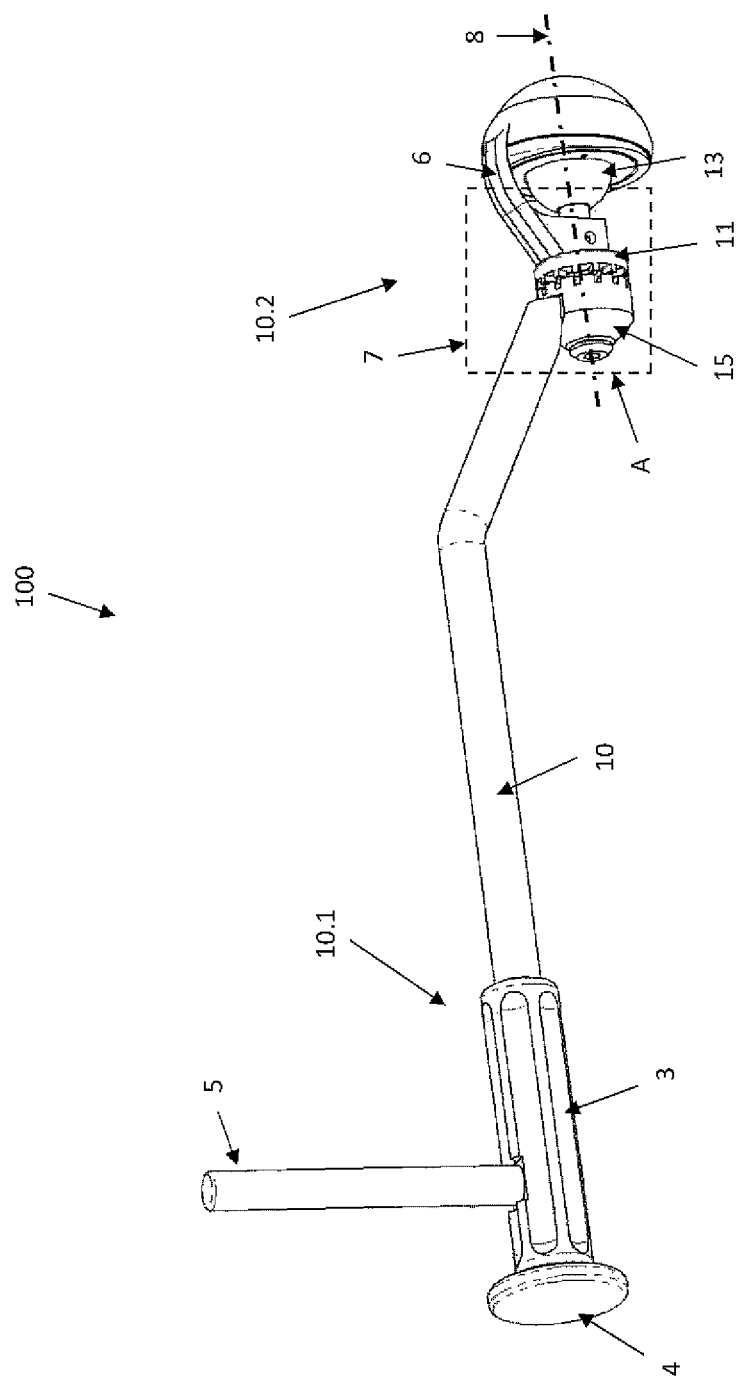
FIG. 1 is a side elevation view of the device for removing an acetabular cup.

For the purpose of removing the acetabular cup, removal instruments have been designed that can help the surgeon with this task. An example of what is known in the state of the art is the device disclosed in U.S. Pat. No. 6,565,575 to Lewis, assigned to Zimmer, Inc. The device substantially has a central, almost rectilinear and elongated, shape, having two ends, to one of which a handle is connected transversal thereto, while at the other there are connection means adapted to detachably connect a hemisphere and a blade. While removing the acetabular cup, the hemisphere is inserted into the acetabular cup so that the blade of the device is forced to penetrate between the external part of the acetabular cup and the patient's bone structure.

To proceed with the insertion, the surgeon must place the instrument in a position such that the end on which the hemisphere and blade are provided penetrates into the incision made in the patient. Such a position will hence be angled as little as possible with respect to the patient's body, so as to approach the acetabular site as frontally as possible in order to make the hemisphere line up with the acetabular cup to be removed. This technique brings the central body of the instrument disclosed by U.S. Pat. No. 6,565,575 towards the patient's wound, potentially coming into contact with it. Hence, by acting on the transverse handle to the central body, the surgeon imposes a rotation on the instrument and, therefore, causes the blade to rotate about the external perimeter of the implanted acetabular cup, separating it from the bone and allowing its removal. This procedure naturally also places in rotation the central body of the instrument which, being in the immediate vicinity of the wound, can cause interference making it rather difficult for the surgeon to operate the rotation freely. Hence, it is necessary, in order to minimize contact between the instrument and the patient's body as much as possible, for the surgeon to work with great caution. Furthermore, it may not be possible to perform a complete revolution of the instrument about its axis in order to completely detach the acetabular cup from its site, it is necessary to remove the instrument from the wound and reposition it so as to proceed with the necessary resection operations.

As can be appreciated, according to the size of the patient, the dimensions of the implanted acetabular cup(s) will vary and, still as a consequence of that, the dimensions of the hemisphere coupled thereto during its removal steps will also have to vary. In order to provide an instrument that is as suitable as possible for the characteristic dimensions of the acetabular cup to be removed, document U.S. Pat. No. 6,565,575 provides a device for removing an acetabular cup wherein both the hemispherical head and the blade can be removed and changed according to the size of the acetabular cup to be removed.

Another example is disclosed in U.S. Pat. No. 7,998,146 to Anderson, assigned to Innomed Inc. In the document, a device is disclosed having a substantially similar shape to that described in document U.S. Pat. No. 6,565,575, also having a removable hemispherical head, interchangeable according to the size of the acetabular cup to be replaced and a fixed blade for the removal of the acetabular cup.

However, what is known in the state of the art has some disadvantages. A disadvantage of what is known in the state of the art, as previously mentioned, is the difficulty to maneuver known devices during operations that imply minimally invasive techniques. In fact, during such surgical operations the aim is to operate on the patient making cuts in the tissues that are as small as possible.

Hence, it appears clear that a device such as those known in the state of the art forces the surgeon, during acetabular cup removal operations, to maneuver in quite restricted spaces with the risk of bringing the known instrument into contact with the patient's soft tissues. Not only, but another disadvantage presented by what is known in the state of the art is the difficulty to make the blade intended for the removal of the acetabular cup perform the necessary revolution movement, in order to completely detach the cup from its position. In fact, still due to the reduced movement possibilities imposed by the minimally invasive surgical techniques, in order to perform a complete revolution of the device about its axis, the surgeon is forced to maneuver the instrument outside the wound or to perform the movements with great caution should they be performed within the surgical site provided in the patient's body, in order to prevent contact between the soft tissues and the known device as far as possible, the contact being able to cause damage to the patient.

Therefore, during the operation, the surgeon runs the risk of having to make a larger cut in order to have sufficient maneuvering space with the consequent unnecessary cutting of the patient's soft tissues. Furthermore, during the acetabular cup removal operations, there may be a risk of inadvertently inflicting small traumas to the tissues surrounding the acetabulum. It is also common surgical experience that during surgery of this kind, it is not at all easy to insert the necessary instrumentation into the patient's body, especially when it requires precise alignment with the bone structure. In fact, the presence of soft tissues, fat and bleeding tissues makes it particularly difficult for the surgeon to correctly identify the correct site for placement of the necessary instrumentation. This, inevitably, causes stress and fatigue for the surgeon and extends the time required for the operation with the resulting increased risks for the patient's health and higher costs for the health facilities.

The above listed disadvantages, due to the conformation of what is known in the state of the art, complicate, as mentioned, the surgical operations, imposing long and unnecessary surgical times, with the consequent inconveniences for patients, the hospital facility and the surgeons. These related disadvantages imply higher costs and lower effectiveness in implementing the operations.

Starting from the notion of these disadvantages, the present invention intends to provide a remedy for them. An object of the present invention is to provide a device for removing an acetabular cup that can be used during minimally invasive surgical operations. Another object of the present invention is to provide a device for removing an acetabular cup that prevents, as far as possible, contact with the soft tissues surrounding the surgical site. A further object of the present invention is to provide a device for removing an acetabular cup that can facilitate the surgical operations preventing unnecessary movements when the device according to the present invention is placed in the patient's body.

Yet another object of the present invention is to provide a device as specified that makes the acetabular cup removal operations quicker. It will also be an object of the present invention to provide a device for removing an acetabular cup that is comfortable to use, easy to make and has contained dimensions and reduced costs.

In the drawing, 100 indicates, as a whole, a device for removing an acetabular cup according to the present invention. The device 100 for removing an acetabular cup comprises: a central body 10, having an elongated substantially cylindrical section shape, made of rigid material, preferably metal or plastic, and having a first free end 10.1 and a second end 10.2 integrally connected to it. The first free end 10.1 comprises a first handle 3, integrally and coaxially provided at the first free end 10.1 of the central body 10 and made of a material, for example, metal or rubber, so as to provide a comfortable and safe grip for the user and a second handle 5, having a cylindrical shape, made of metal and/or plastic material and assembled on the first handle 3 transversally to the axis of the central body 10, so as to form a single body therewith. The free end 10.1 has, in its end part, an area with a larger section 4, known as an impact area, placed downstream of the first handle 3, made of shock-resistant material suitable for withstanding impulse stress of a notable intensity. The second end 10.2 has a cylindrical section and central axis not coinciding with the central axis of the central body 10.

Figure 2:
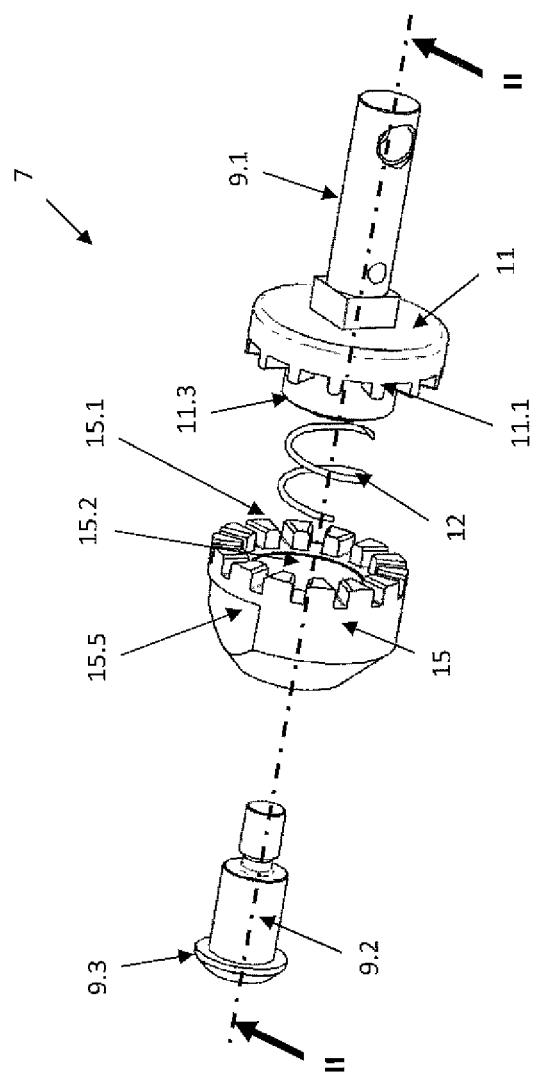
FIG. 2 is a detailed view of detail A of FIG. 1.

In an embodiment illustrated in the drawing by way of example, the central axis of the central body 10 and the central axis of the second end 10.2 form an angle comprised between 0 and 90 degrees, for example, 30 degrees. Naturally, the angle illustrated in the exemplificative figures does not preclude the possibility of making the device 100 with different angulations, or, potentially, central coinciding axes, without however departing from the scope of protection of the present invention. The second end 10.2 further comprises a ratchet device 7. The ratchet device 7, represented in exploded view in FIG. 2, has a first toothed element 15, the toothed cup-shaped element having a substantially cylindrical and symmetrical shape with respect to its central axis 8, hollow inside and having a surface comprising a plurality of teeth 15.1 frontally projecting from it. The toothed cup-shaped element 15 is axially fitted onto a portion 9.2 of a shaft 9, coaxial thereto, and is free to turn idle on the portion 9.2 of the shaft 9.

Furthermore, the toothed cup-shaped element 15 has a coupling area 15.5 adapted to make the toothed cup-shaped element 15 integral with the second end 10.2 of the central body 10, for example, by welding. In front of the toothed cup-shaped element 15, a second toothed element 11 is arranged, having a substantially cylindrical shape, complementary to the toothed cup-shaped element 15 and substantially symmetrical with respect to one of its central axes. The toothed element 11 comprises a central relief area 11.3, having a substantially cylindrical shape, axially projecting from the toothed element 11 and of dimensions such as to be inserted in an axial cavity 15.3 provided in the toothed cup-shaped element 15.

The toothed element 11 is further partially fitted onto and integrally connected to a portion 9.1 of the shaft 9. The portion 9.1 of the shaft 9 is positioned axially with respect to the toothed element 11 and is adapted to be coupled with respective portion 9.2 of the shaft 9 provided detachably coupled with the toothed cup-shaped element 15. A surface having a plurality of teeth 11.1 is radially provided on the surface of the element 11 and axially projecting from it, facing the toothed cup-shaped element 15, and is made so as to be able to mesh in the surface with the plurality of teeth 15.1 of the toothed cup-shaped element 15.

Figure 3:
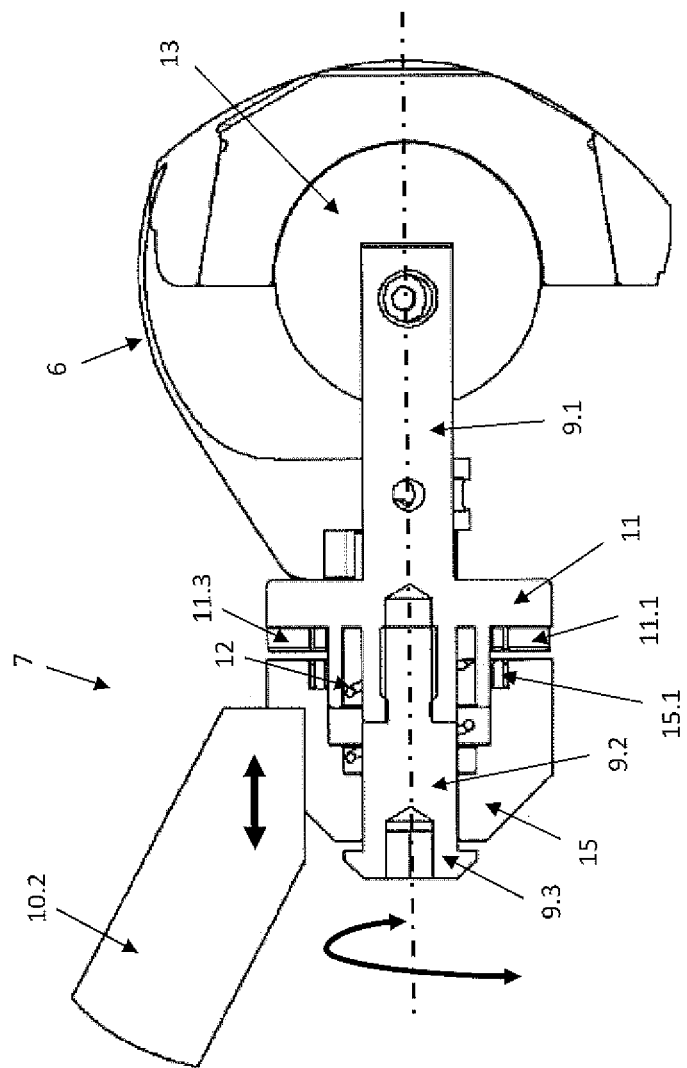
FIG. 3 is a sectional view of FIG. 2 according to section line II-II.

Between the toothed cup-shaped element 15 and the toothed element 11, an elastic means 12 is interposed, for example, a helical spring, housed within the axial cavity 15.2, fitted onto the shaft 9 and interposed between the bottom wall of the axial cavity 15.2 and the central relief area 11.3. Note that, in the embodiment illustrated, the axial cavity 15.2 has a through hole in its bottom wall to house the shaft 9 onto which the helical spring 12 is fitted as can be seen in FIG. 3. In the end part of the portion 9.2 of the shaft 9, an abutment 9.3 is provided to prevent the accidental withdrawal of the portion 9.2 of the shaft 9 from the toothed cup-shaped element 15. When the device is in the operating configuration, the two portions 9.1 and 9.2 of the shaft 9 are integrally coupled, for example, through a snap coupling. Note also that, as represented in the drawings provided by way of example and as described above, in order to optimize explanatory clarity, an embodiment has been illustrated wherein the shaft 9 is equipped, as mentioned, with two portions 9.1 and 9.2 adapted to be coupled to one another.

Naturally, it will be possible to provide an embodiment wherein the shaft 9 is made of a single body, without departing from the scope of protection of the present invention. Note again that, in the embodiment presented by way of example in the drawings, the toothed cup-shaped element 15 and the toothed element 11 are coaxial but it a person skilled in the art will appreciate that they could have axes that do not coincide in some embodiments.

At the free end of the portion 9.1 of the shaft 9, a cutting element 6 is provided, for example, a blade, and a stop element 13, for example, a spherical or hemispherical head. The blade 6 is assembled on the portion 9.1 of the shaft 9, for example, through a threaded coupling or through a fixing pin, and is able to rotate integrally with the shaft 9. Likewise, the head 13 is assembled integrally onto the portion 9.1 of the shaft 9 through, for example, a spring positioner.

Operation

During the steps for removing an acetabular cup through the anterior approach technique, the surgeon, having conveniently pre-treated the area around the acetabulum, inserts the device 100 for removing an acetabular cup according to the present invention into the patient's body. The conformation of the central body 10 is such that, when the surgeon grips the device 100 keeping the second handle 5 projecting from the opposite side of the central body 10 with respect to the patient, the only part of the device 100 that is in contact with the aforementioned patient's body comprises the ratchet 7, the head 13 and the blade 6. When the surgeon inserts the device 100 into the patient's body, the conformation of the central body 10 also allows the head 13 to be easily inserted into the acetabular cup to be removed. This takes place since the central axis of the central body 10 and the central axis 8 do not coincide. In fact, the non-coincidence between the aforementioned axes makes it possible to keep the central body 10 and, consequently, the handles 3 and 5, at a maneuvering distance from the patient's body and to place in contact therewith only the parts of the device 100 strictly necessary for the removal of the acetabular cup. In fact, by inserting the head 13 in the acetabular cup to be removed, the blade 6 is located in the area pre-treated by the surgeon surrounding the acetabular cup to be removed. At this point, by acting on the system of handles 3 and 5 provided at the first end 10.1 of the central body 10 and pushing the first end 10.1 towards the head 13 the toothed cup-shaped element 15 is meshed with the toothed element 11.

This meshing takes place thanks to the rigid structure presented by the central body 10 and its two ends 10.1 integral with the handles 3 and 5, and 10.2 integral with the toothed cup-shaped element 15. A rigid structure transfers the pressure exerted by the surgeon on the toothed cup-shaped element 15, varying its configuration from a first position, known as the rest position. The toothed cup-shaped element 15 is not meshed with the toothed element 11, to a second position, known as the meshed position, and the toothed cup-shaped element 15 is meshed with the toothed element 11. When the pressure made by the surgeon is transmitted to the toothed cup-shaped element 15 forcing it into the meshed position, the toothed cup-shaped element 15 transfers the pressure onto the spring 12, placing it in compression and controlling its deformation.

The deformation of the spring 12 makes it possible for the toothed cup-shaped element 15 to approach the toothed element 11, hence bringing the surface comprising the plurality of teeth 15.1 to mesh with the surface comprising the plurality of teeth 11.1. Therefore, by acting for example, on the handle 5 and placing it in rotation, for example, clockwise, the toothed cup-shaped element 15, being integral with the second end 10.2 of the central body 10, is made to rotate clockwise due to the toothed coupling with the toothed element 11. The toothed element 11, placed in rotation, in turn, causes a similar rotation on the blade 6, it being integral with the teethed surface element 11 through the portion 9.1 of the shaft 9.

The rotation will be limited by the free rotation of the second end 10.2 before it comes into contact with the patient's soft tissues. When the end 10.2 almost reaches contact with the patient's the soft tissues, the surgeon removes the pressure exerted on the handle 5 and, consequently, transferred to the ratchet 7 through the central body 10 by means of its two ends 10.1 and 10.2. The compression strain having been removed, the spring 12 no longer kept in the compressed configuration by the pressure, regains its neutral configuration by reciprocally moving the toothed cup-shaped element 15 away from the toothed element 11, releasing the surfaces comprising the pluralities of teeth s 15.1 and 11.1 from their meshed configuration illustrated above. At this point, the surgeon can, if further rotation of the blade 6 is required in order to extract the acetabular cup from its site in the patient's body, impose a rotation in the opposite direction to the one performed previously, for example, in the anti-clockwise direction, bringing the handles 3 and 5 back to the initial configuration.

The counter rotation, as illustrated, does not have an effect on the position of the blade, keeping it in the position reached when the pressure on the handles is stopped. Note that the counter rotation imposed by the surgeon on the system of handles 3 and 5 will also have an effect on the second end 10.2, bringing it back into a position of non-interference with the soft tissues. At this point, the surgeon will repeat the actions listed above to place the surfaces comprising the pluralities of teeth 15.3 and 11.3 provided on the toothed cup-shaped element 15 and the toothed element 11, in contact again and, imposing a rotation, for example, clockwise, along with a pressure, place the blade 6 in rotation. The above listed operations will be repeated until the acetabular cup to be removed has been completely taken out of its site.

As appears clear from the above description, the present invention provides a device 100 for removing an acetabular cup that advantageously achieves the aforementioned objects. In fact, as is appreciated by the person skilled in the art, the device 100 for removing an acetabular cup can be used in minimally invasive surgery since the only part subject to insertion in the patient's body is the portion formed by the ratchet 7, the head 13 and the blade 6. Furthermore, after placement of the device 100 for removing an acetabular cup, it is possible for the surgeon to act on the instrument without touching the soft tissues with a part of the central body 10 and/or with a part of its second end 10.2 proximal to the central body 10. Unlike what is known in the state of the art, the blade 6 can perform a complete revolution about the axis 8 visible in FIG. 1 without it being necessary to extract the device 100 to reposition the central body in order to prevent contact with the soft tissues, so as to have enough space to maneuver in order to act on the handles 3 and 5.

Naturally numerous variants can be made to what is described and illustrated merely by way of non-limiting example, without for this reason departing from the protective scope of the present invention and therefore from the domain of the present industrial patent.

The invention claimed is:

1. A device for removing an acetabular cup, the device comprising:
   a central body having
   a first end integrally connected to said central body, bearing a first handle, integrally and coaxially provided at said first free end of the central body, and a second handle attached to said first handle, said second handle being transverse to a central axis of the central body, and
   a second end integrally connected to said central body
   a first toothed cup-shaped element, integral with the second end of the central body;
   a second toothed element, arranged in front of said toothed cup-shaped element, complementary to said toothed cup-shaped element and substantially symmetrical with respect to one of its central axes, wherein the first tooth cup-shaped element and the second toothed element are detachably couplable to one another and, when coupled, rotation of the first tooth cup-shaped element in a predetermined direction causes rotation of the second toothed element;
   a cutting element; and
   a stop element which can be detachably coupled to the second toothed element.

2. The device for removing an acetabular cup as claimed in claim 1 wherein at least one of said first toothed cup-shaped element and said second toothed element has a central axis which does not coincide with the central body.

3. The device for removing an acetabular cup as claimed in claim 1 further comprising a cutting element and a stop element which can be detachably coupled to a shaft.

4. The device for removing an acetabular cup as claimed in claim 1 wherein the first toothed element is selectively movable between a first rest position and a second meshed position.

5. The device for removing an acetabular cup as claimed in claim 1 further comprising an elastic means arranged between said first toothed cup-shaped element and the second toothed element.

6. The device for removing an acetabular cup as claimed in claim 1 wherein the central axes of said central body and of said end are arranged so as to form an angle of between 0 and 90 degrees.

* * * * *